United States Patent
Katsumata

(10) Patent No.: US 11,364,048 B2
(45) Date of Patent: Jun. 21, 2022

(54) ENERGY TREATMENT DEVICE

(71) Applicant: OLYMPUS CORPORATION, Hachioji (JP)

(72) Inventor: Minoru Katsumata, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 429 days.

(21) Appl. No.: 16/451,358

(22) Filed: Jun. 25, 2019

(65) Prior Publication Data

US 2019/0307503 A1   Oct. 10, 2019

Related U.S. Application Data

(60) Division of application No. 15/391,469, filed on Dec. 27, 2016, now Pat. No. 10,349,969, which is a
(Continued)

(30) Foreign Application Priority Data

Apr. 15, 2014   (JP) .................... 2014-083863

(51) Int. Cl.
*A61B 17/32* (2006.01)
*A61B 17/28* (2006.01)
(Continued)

(52) U.S. Cl.
CPC .. *A61B 17/320092* (2013.01); *A61B 17/2816* (2013.01); *A61B 18/00* (2013.01);
(Continued)

(58) Field of Classification Search
CPC . A61B 18/00; A61B 18/1442; A61B 18/1445; A61B 18/12; A61B 18/1206;
(Continued)

(56) References Cited

U.S. PATENT DOCUMENTS 6,139,561 A * 10/2000 Shibata .......... A61B 17/320092
  606/169
6,165,191 A * 12/2000 Shibata .......... A61B 17/320092
  606/169
(Continued)

FOREIGN PATENT DOCUMENTS

JP   2000000249 A   1/2000
JP   2000041990 A   2/2000
(Continued)

OTHER PUBLICATIONS

Chinese Office Action dated Sep. 28, 2017 issued in counterpart Chinese Application No. 201580002365.0.
(Continued)

*Primary Examiner* — Phong Son H Dang
(74) *Attorney, Agent, or Firm* — Holtz, Holtz & Volek PC

(57) ABSTRACT

An energy treatment device includes a movable handle including a jaw and a first through hole, an elongated member, and a sheath including a hollow portion and a second through hole, wherein the hollow portion is configured to receive the elongated member. The second through hole is configured to extend so as not to overlap with the hollow portion. The movable handle is configured to rotate about an axis which is configured to pass through the first through hole and the second through hole such that the jaw is rotatable with respect to the sheath, and $(D1+D2)/2<L1$ is satisfied, where $D1$ is a diameter of the hollow portion, $D2$ is a diameter of the first through hole, and $L1$ is a distance between a central position of the hollow portion and a central position of the first through hole in an opening/closing direction of the jaw.

5 Claims, 10 Drawing Sheets

Related U.S. Application Data division of application No. 15/060,535, filed on Mar. 3, 2016, now Pat. No. 9,566,084, which is a continuation of application No. PCT/JP2015/056229, filed on Mar. 3, 2015.

(51) Int. Cl.

| | |
|---|---|
| *A61B 18/14* | (2006.01) |
| *A61B 18/00* | (2006.01) |
| *A61B 18/12* | (2006.01) |
| *A61B 17/00* | (2006.01) |
| *A61B 90/00* | (2016.01) |

(52) U.S. Cl.
CPC .......... *A61B 18/12* (2013.01); *A61B 18/1442* (2013.01); *A61B 18/1445* (2013.01); *A61B 18/1206* (2013.01); *A61B 2017/00473* (2013.01); *A61B 2017/320088* (2013.01); *A61B 2017/320094* (2017.08); *A61B 2018/0072* (2013.01); *A61B 2018/00083* (2013.01); *A61B 2018/00922* (2013.01); *A61B 2018/126* (2013.01); *A61B 2090/034* (2016.02); *A61B 2090/035* (2016.02)

(58) Field of Classification Search
CPC ........ A61B 17/320092; A61B 17/2816; A61B 2018/126; A61B 2018/00083; A61B 2018/0072; A61B 2018/00922; A61B 2090/035; A61B 2090/034; A61B 2017/320088; A61B 2017/00473; A61B 2017/320094

See application file for complete search history.

(56) References Cited

U.S. PATENT DOCUMENTS

| | | | | |
|---|---|---|---|---|
| 7,563,269 | B2 | 7/2009 | Hashiguchi | |
| 2004/0193199 | A1* | 9/2004 | Hashiguchi | .... A61B 17/320092 |
| | | | | 606/169 |
| 2007/0032811 | A1* | 2/2007 | Storz | ................. A61B 17/1608 |
| | | | | 606/174 |
| 2007/0191713 | A1* | 8/2007 | Eichmann | .......... A61B 17/2841 |
| | | | | 600/471 |
| 2008/0234708 | A1* | 9/2008 | Houser | .......... A61B 17/320092 |
| | | | | 606/169 |
| 2008/0234711 | A1* | 9/2008 | Houser | .......... A61B 17/320068 |
| | | | | 606/169 |
| 2009/0326531 | A1 | 12/2009 | Geiselhart | |
| 2010/0030248 | A1* | 2/2010 | Palmer | .......... A61B 17/320092 |
| | | | | 606/169 |
| 2010/0057117 | A1 | 3/2010 | Yamada | |
| 2010/0331873 | A1* | 12/2010 | Dannaher | .......... A61B 17/2816 |
| | | | | 606/169 |
| 2012/0179182 | A1* | 7/2012 | Mastri | ............ A61B 17/320092 |
| | | | | 606/169 |
| 2012/0253372 | A1* | 10/2012 | Ross | .............. A61B 17/320092 |
| | | | | 606/169 |
| 2012/0296356 | A1* | 11/2012 | Balan | .............. A61B 17/320092 |
| | | | | 606/169 |
| 2013/0110155 | A1* | 5/2013 | Tsuchiya | ............. A61B 17/2816 |
| | | | | 606/205 |
| 2013/0218185 | A1* | 8/2013 | Sanai | ....................... A61N 7/00 |
| | | | | 606/169 |
| 2015/0080925 | A1* | 3/2015 | Schulte | ................ A61B 17/285 |
| | | | | 606/169 |
| 2015/0142031 | A1* | 5/2015 | Faller | .................... A61B 90/70 |
| | | | | 606/169 |

FOREIGN PATENT DOCUMENTS

| | | |
|---|---|---|
| JP | 2001037769 A | 2/2001 |
| JP | 2004209042 A | 7/2004 |
| JP | 2004283617 A | 10/2004 |
| JP | 2010505476 A | 2/2010 |
| JP | 2012531970 A | 12/2012 |
| WO | 2012128362 A1 | 9/2012 |
| WO | 2015041846 A2 | 3/2015 |
| WO | 2015073428 A1 | 5/2015 |
| WO | 2015094746 A1 | 6/2015 |

OTHER PUBLICATIONS

Ethicon Launches Harmonic Focus+ Shears With Adaptive Tissue Technology at IFHNOS/AHNS Scientific Meeting.
Ethicon Receives 510(K) Clearance for New Harmonic Focus+ Shears With Adaptive Tissue Technology.
Extended European Search Report (EESR) dated Nov. 7, 2017 issued in counterpart European Application No. 15779907.3.
International Search Report (ISR) dated Jun. 9, 2015 issued in International Application No. PCT/JP2015/056229.

\* cited by examiner

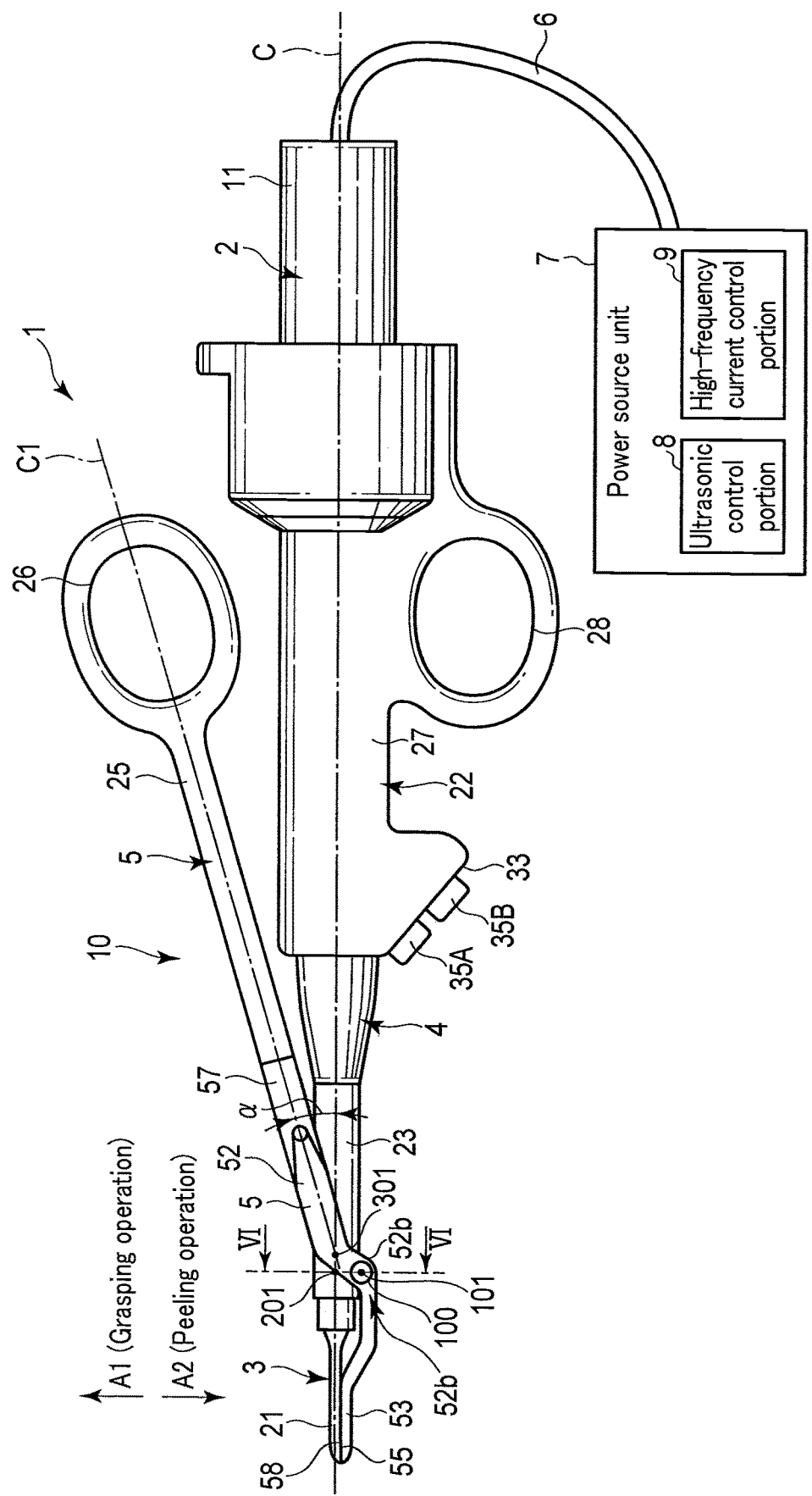
F I G. 1

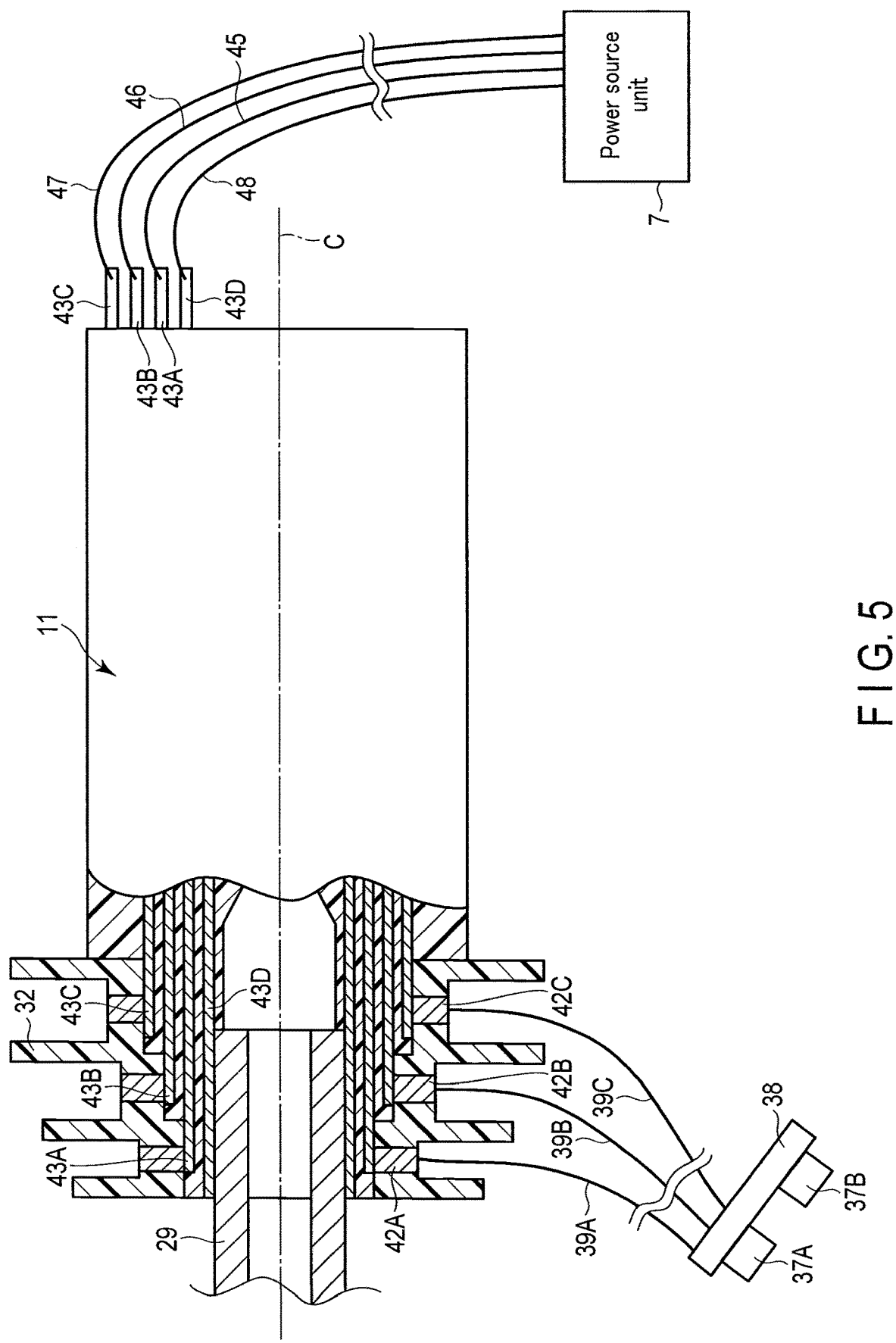
F I G. 5

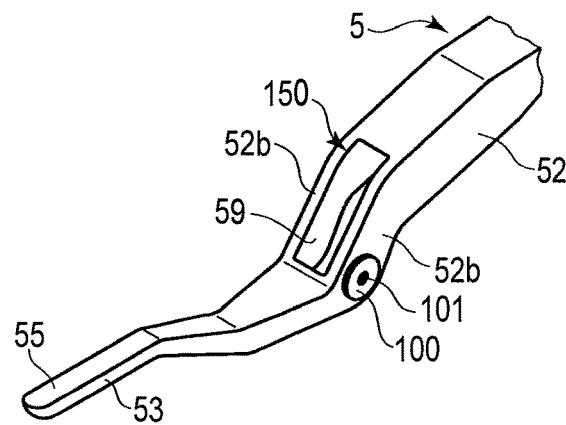
F I G. 9A
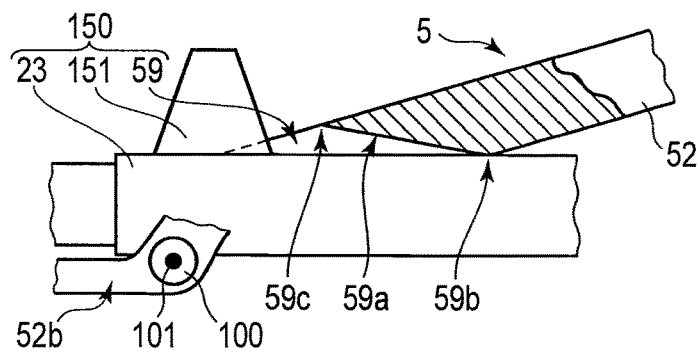
F I G. 9B
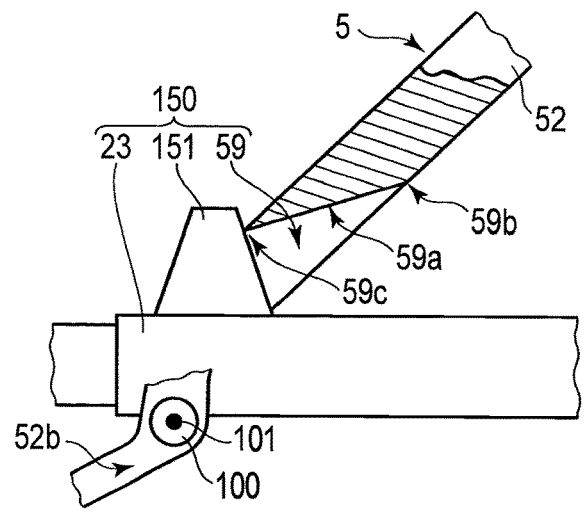
F I G. 9C

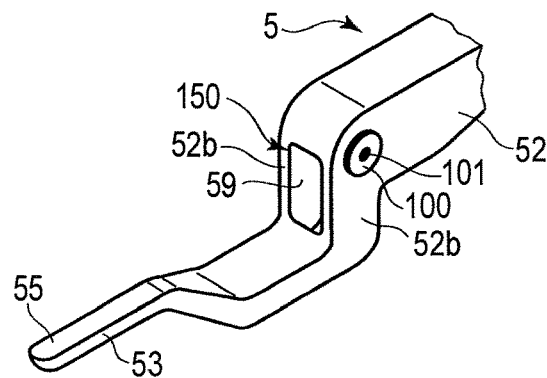
F I G. 10A
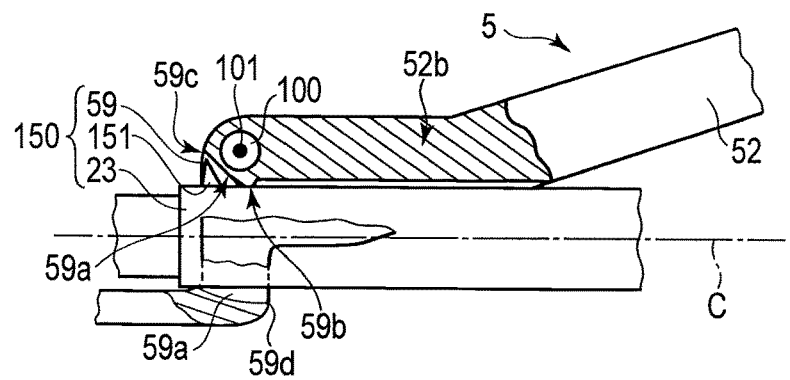
F I G. 10B
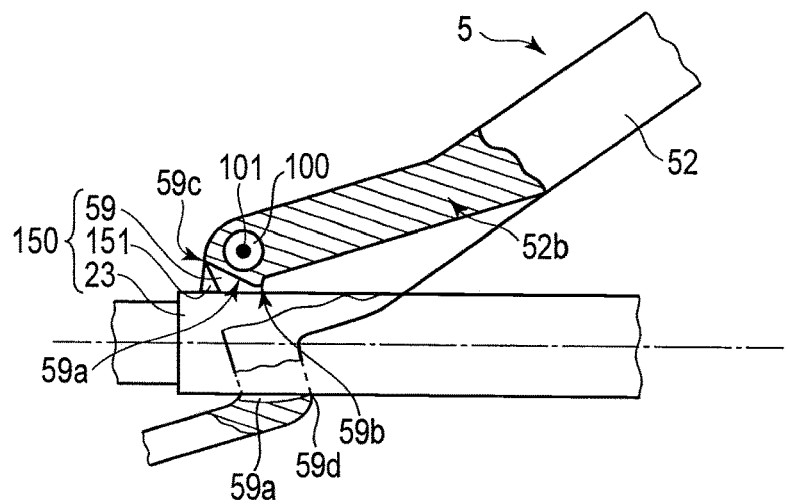
F I G. 10C

ENERGY TREATMENT DEVICE

CROSS-REFERENCE TO RELATED APPLICATIONS

This application is a Divisional Application of U.S. Ser. No. 15/391,469, filed Dec. 27, 2016, which is a Divisional application of U.S. Ser. No. 15/060,535, filed Mar. 3, 2016 (now U.S. Pat. No. 9,566,084 issued Feb. 14, 2017), which is a Continuation Application of PCT Application No. PCT/JP2015/056229, filed Mar. 3, 2015 and based upon and claiming the benefit of priority from prior Japanese Patent Application No. 2014-083863, filed Apr. 15, 2014, the entire contents of all of which are incorporated herein by reference.

BACKGROUND OF THE INVENTION

1. Field of the Invention

The present invention relates to a forceps type of energy treatment device in which a movable handle is opened and closed to a fixed handle, thereby opening and closing a distal end portion of a jaw to a distal end portion of a probe.

2. Description of the Related Art

For example, Jpn. PCT National Publication No. 2012-531970 discloses a forceps type of energy treatment device having a probe. This treatment device has the probe to be inserted into a sheath and a jaw openable and closable to the probe. The sheath and the probe are extended along a longitudinal axis. The jaw is attached to a distal end portion of the sheath so that the jaw is rotatable (openable and closable) around an opening/closing axis. The opening/closing axis is provided perpendicularly to the longitudinal axis. The above attaching is performed by a pair of bearings or the like provided between an outer peripheral surface of the sheath and an inner peripheral surface of the jaw.

A distal end portion of the jaw closes to a distal end portion of the probe so that the distal end portion of the jaw and the distal end portion of the probe sandwich a treatment object such as a biological tissue therebetween to grasp the treatment object. The distal end portion of the jaw opens to the distal end portion of the probe so that the distal end portion of the jaw and the distal end portion of the probe are pushed into, e.g., the treatment object to expand and peel off the treatment object.

BRIEF SUMMARY OF THE INVENTION

An aspect of an energy treatment device of the present invention including a longitudinal probe that transmits an ultrasonic vibration; a distal end portion that is provided on a distal end side of the probe and treats a treatment object by the ultrasonic vibration; a sheath that has a hollow portion and a distal end and the distal end portion projects from the distal end in a state where the probe is inserted into the hollow portion; a fixed handle that is provided in a proximal end portion of the sheath and on which an operator places a first finger; a movable handle that has, on a proximal side, a finger placing portion on which the operator places a second finger, and that has, on a distal side, a jaw which grasps the treatment object together with the distal end portion; a jaw side through hole portion that is provided in the movable handle and formed between the finger placing portion and the jaw; a sheath side through hole portion that is provided in the sheath and provided at a position at which the sheath side through hole portion does not overlap with the hollow portion; and an opening/closing axis member that is inserted in the jaw side through hole portion and the sheath side through hole portion to openably and closably attach the movable handle to the fixed handle.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of a medical treatment apparatus according to a first embodiment of the present invention;

FIG. 5 is a schematic view showing an electric connection state in a transducer case, a cylindrical member and an electric connection ring;

FIG. 9A is a perspective view of a jaw shown in FIG. 1 of the first embodiment, and a view showing a regulating mechanism according to a second embodiment;

FIG. 9B is a view showing a state where the regulating mechanism according to the second embodiment regulates an opening/closing angle α so that the opening/closing angle α of a movable handle to a fixed side is minimize, and the regulating mechanism according to the second embodiment positioned the minimum closing position of the movable handle;

FIG. 9C is a view showing a state where the regulating mechanism according to the second embodiment regulates the opening/closing angle α so that the opening/closing angle α of the movable handle to the fixed side is maximize, and the regulating mechanism according to the second embodiment positioned the maximum opening position of the movable handle;

FIG. 10A is a perspective view of a jaw shown in FIG. 7A in the first embodiment, and is a view showing a regulating mechanism according to a modification of the second embodiment;

FIG. 10B is a view showing a state where the regulating mechanism according to the modification of the second embodiment regulates the opening/closing angle α of the movable handle to the fixed side is minimize, and the regulating mechanism according to the modification of the second embodiment positioned the minimum closing position of the movable handle; and FIG. 10C is a view showing a state where the regulating mechanism according to the modification of the second embodiment regulates the opening/closing angle α so that the opening/closing angle α of the movable handle to the fixed side is maximize, and the regulating mechanism according to the modification of the second embodiment positioned the maximum opening position of the movable.

DETAILED DESCRIPTION OF THE INVENTION

Figure 2:
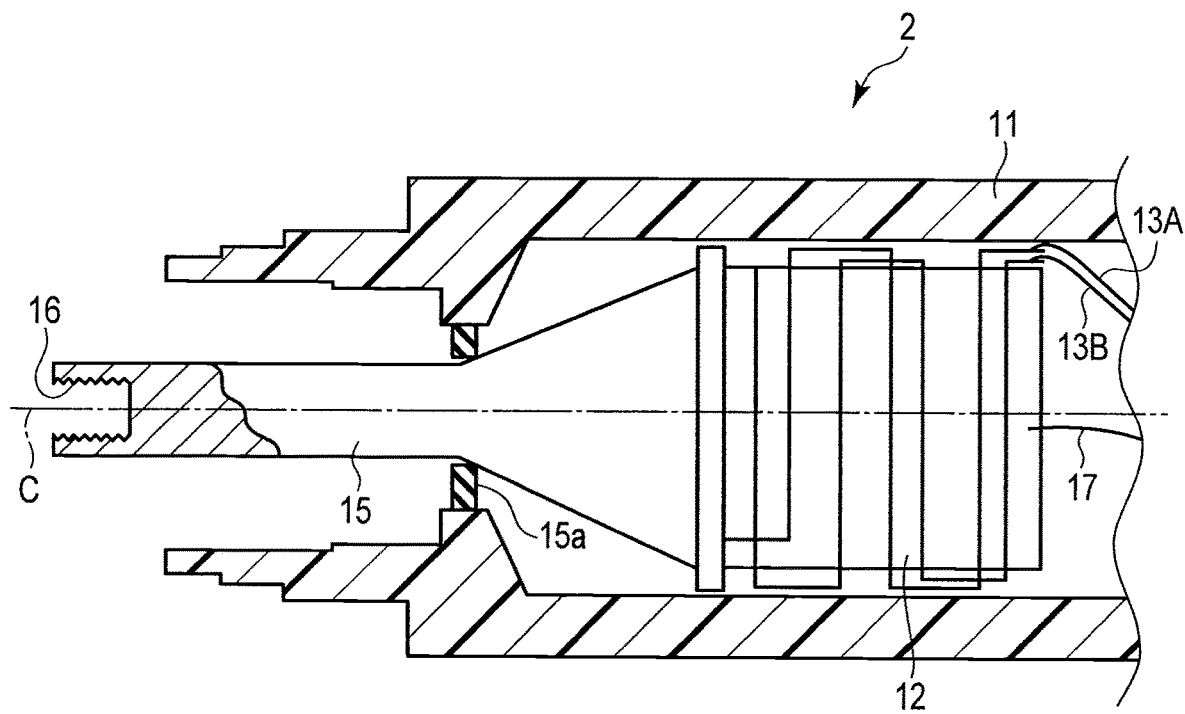
FIG. 2 is a cross-sectional view showing a configuration of a transducer unit.

Hereinafter, embodiments of the present invention will be described in detail with reference to the drawings.

First Embodiment

[Configuration]

A first embodiment will be described with reference to FIG. 1, FIG. 2, FIG. 3, FIG. 4, FIG. 5 and FIG. 6. In some of the drawings, some of the members are omitted for clarification of the drawings.

[Medical Treatment Apparatus 1]

A medical treatment apparatus 1 shown in FIG. 1, sandwiches a treatment object such as a biological tissue to grasp the treatment object by a first electrode portion 21 that functions as a distal end portion of a probe 3 and a second electrode portion 53 that functions as a distal end portion of a jaw 52, in the probe 3 and the jaw 52 to be provide in an after-mentioned energy treatment device (hereinafter referred to as a treatment device 10). The grasping is performed when the second electrode portion 53 is closed (brought close) to the first electrode portion 21. Further, the medical treatment apparatus 1 is capable of treating the grasped treatment object by, e.g., energy of an ultrasonic wave, a high frequency, heat or the like. The medical treatment apparatus 1 is a grasping treatment apparatus. It is to be noted that the medical treatment apparatus 1 of the present embodiment is also used as a bipolar treatment apparatus that treats by a high-frequency current by use of the distal end portion of the probe 3 and the jaw 52 as electrodes. The medical treatment apparatus 1 is also used as an ultrasonic treatment apparatus that treats by an ultrasonic vibration.

The medical treatment apparatus 1 peels off the treatment object by the distal end portion of the probe 3 and the jaw 52 which are pushed into the treatment object. The peeling is performed when the second electrode portion 53 opens (comes away) from the first electrode portion 21.

As shown in FIG. 1, the medical treatment apparatus 1 has a power source unit 7 that functions as a supplying unit to supply electric power for the energy, and the treatment device 10 that treats the treatment object by the energy supplied from the power source unit 7.

[Power Source Unit 7]

As shown in FIG. 1, the power source unit 7 has an ultrasonic control portion 8 that controls a current for the ultrasonic vibration, a high-frequency current control portion 9 that controls the current for the high frequency, and a cable 6 that electrically connects the ultrasonic control portion 8 to the treatment device 10 and electrically connects the high-frequency current control portion 9 to the treatment device 10. One end of the cable 6 is connected to the power source unit 7, and the other end of the cable 6 is connected to a proximal end of a transducer case 11 which will be described later.

[Treatment Device 10]

As shown in FIG. 1, the treatment device 10 has a transducer unit 2, the probe 3, a sheath unit 4, and a movable handle unit 5. The transducer unit 2, the probe 3 and the sheath unit 4 are on a fixed side, and the movable handle unit 5 is a movable side that is rotatably movable to the fixed side.

[Transducer Unit 2]

As shown in FIG. 1 and FIG. 2, the transducer unit 2 has the transducer case 11. As described above, the proximal end of the transducer case 11 is connected to an end portion of the cable 6.

As shown in FIG. 2, the transducer unit 2 has an ultrasonic transducer 12 provided in the transducer case 11. The ultrasonic transducer 12 has a piezoelectric element that converts the current supplied from the ultrasonic control portion 8 into the ultrasonic vibration.

The ultrasonic transducer 12 is connected to one end of each of electric signal lines 13A and 13B. The electric signal lines 13A and 13B are provided in the cable 6. Further, the other end of each of the electric signal lines 13A and 13B is connected to the ultrasonic control portion 8. The current is supplied from the ultrasonic control portion 8 to the ultrasonic transducer 12 via the electric signal lines 13A and 13B, thereby generating the ultrasonic vibration in the ultrasonic transducer 12.

The ultrasonic transducer 12 is connected to one end of an electric signal line 17 separately from the electric signal lines 13A and 13B. The electric signal line 17 is provided in the cable 6. Further, the other end of the electric signal line 17 is connected to the high-frequency current control portion 9.

The electric signal lines 13A, 13B and 17 are included in the cable 6.

As shown in FIG. 2, the transducer unit 2 further has a horn 15 that enlarges an amplitude of the ultrasonic vibration generated in the ultrasonic transducer 12. The horn 15 is coupled with a distal end of the ultrasonic transducer 12 so that the horn 15 is positioned at the distal end of the ultrasonic transducer 12.

The horn 15 is attached to the transducer case 11 via an insulating member 15a, and electrically insulated from the transducer case 11 by the insulating member 15a. The horn 15 has an internal thread portion 16 formed in a distal end portion of the horn 15.

[Probe 3]

Figure 3:
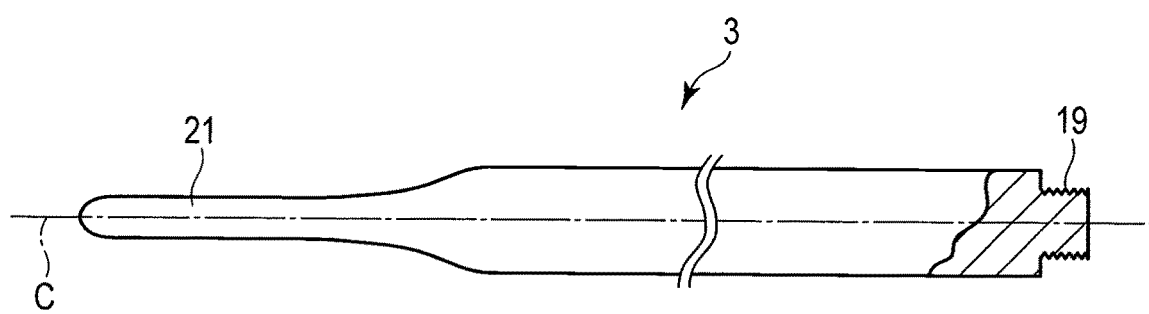
FIG. 3 is a side view including a partial cross section of a probe.

As shown in FIG. 3, the probe 3 is provided along a longitudinal axis C. The longitudinal axis C functions as a central axis of the probe 3. The probe 3 has a columnar shape. The probe 3 has an external thread portion 19 formed in a proximal end portion of the probe 3 to be screwed into the internal thread portion 16.

The probe 3 is attached to the horn 15 by the screwing. In consequence, the ultrasonic vibration generated in the ultrasonic transducer 12 is transmitted to a distal end of the probe 3 via the horn 15 and the probe 3. That is, the ultrasonic vibration is transmitted from a proximal end of the probe 3 to the distal end of the probe 3. It is to be noted that the ultrasonic vibration is a vertical vibration in which a transmitting direction of the vibration matches a vibrating direction.

The probe 3 is attached to the horn 15, whereby a probe side current path of a high-frequency current is formed from the high-frequency current control portion 9 through the electric signal line 17, the ultrasonic transducer 12 and the horn 15 to a distal end portion of the probe 3. The probe side current path indicates a path through which the high-frequency current flows. The probe 3 has the first electrode portion 21 that functions as the distal end portion of the probe 3. That is, the high-frequency current is transmitted along the longitudinal axis C between the high-frequency current control portion 9 and the first electrode portion 21 through the probe side current path.

[Sheath Unit 4]

As shown in FIG. 1, the sheath unit 4 is extended along the longitudinal axis C. The sheath unit 4 has a fixed handle 22 and a sheath 23 attached to a distal end of the fixed handle 22.

Figure 4:
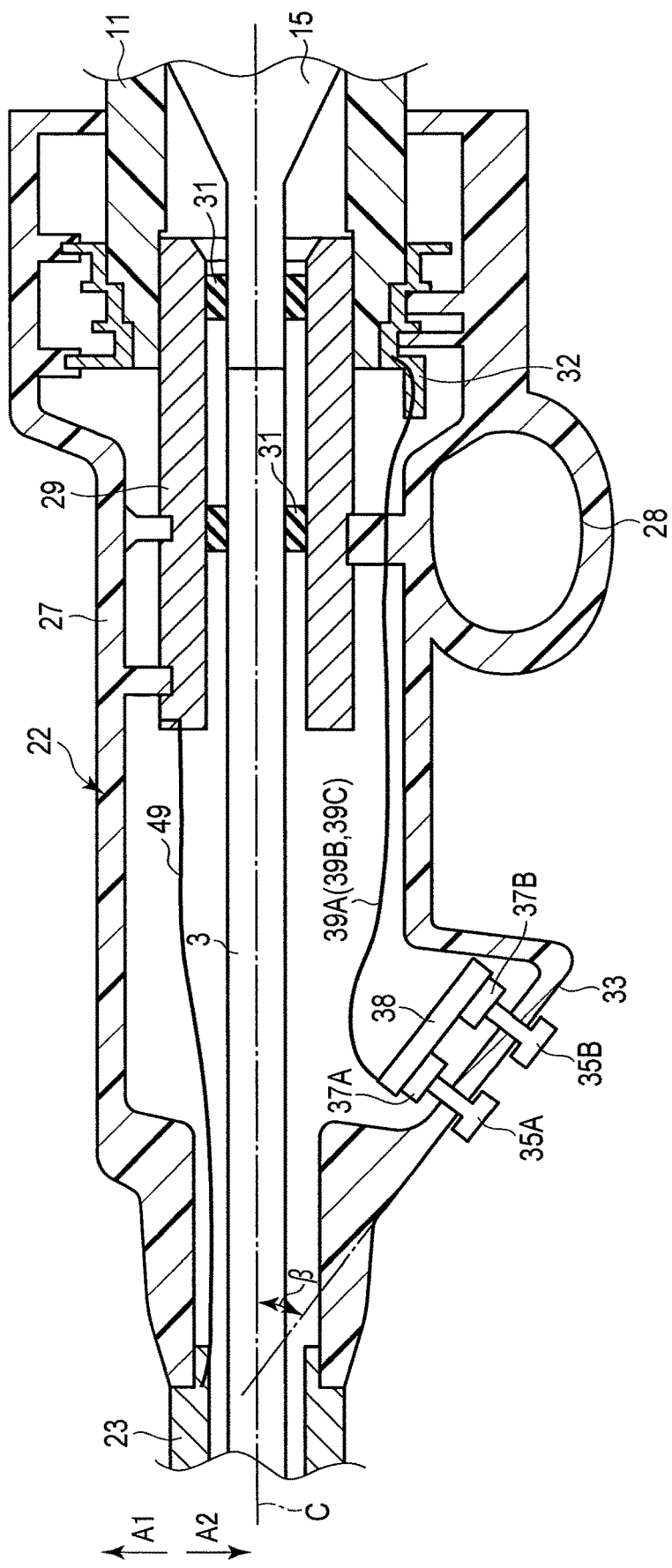
FIG. 4 is a schematic cross-sectional view showing an inner configuration of a fixed handle.

As shown in FIG. 1 and FIG. 4, the fixed handle 22 has a handle casing 27 that functions as an exterior portion. The handle casing 27 has a fixed handle ring 28 that is provided in a part on the side of an after-mentioned second direction of the handle casing 27 and that functions as a fixed side finger placing portion. The fixed handle ring 28 projects toward a second direction to the longitudinal axis C. In the second direction, the fixed handle ring 28 is provided on an outer side to an opening/closing axis member 100 that will be described later.

As shown in FIG. 4, the handle casing 27 has a cylindrical member 29 provided in the handle casing 27 and fixed to the handle casing 27. The proximal end of the probe 3 is extended into the cylindrical member 29. In the cylindrical member 29, the probe 3 is attached to the horn 15 as described above. The cylindrical member 29 supports the probe 3 and the horn 15 via insulating members 31. In consequence, the probe 3 and the horn 15 are prevented from coming in contact with the cylindrical member 29, and the probe 3 and the horn 15 are electrically insulated from cylindrical member 29.

On an outer peripheral side of the cylindrical member 29, an electric connection ring 32 is provided. The electric connection ring 32 is provided to be fixed to an inner peripheral surface of the handle casing 27. A distal end portion of the transducer case 11 is engaged between the cylindrical member 29 and the electric connection ring 32. The distal end portion of the transducer case 11 is engaged in between the cylindrical member 29 and the electric connection ring 32, whereby the transducer case 11 is coupled with the fixed handle 22 (the sheath unit 4 and the handle casing 27). In a state where the transducer case 11 is coupled with the fixed handle 22, an outer peripheral portion of the distal end portion of the transducer case 11 comes in contact with the electric connection ring 32, and an inner peripheral portion of the distal end portion of the transducer case 11 comes in contact with the cylindrical member 29.

As shown in FIG. 1 and FIG. 4, the handle casing 27 has an inclined flat surface 33 provided in a part on the side of the second direction (the direction of an arrow A2 shown in FIG. 1 and FIG. 4) of the handle casing 27 (the fixed handle 22) and inclined to the longitudinal axis C. The inclined flat surface 33 is provided on a distal end direction side to the fixed handle ring 28. The inclined flat surface 33 is positioned on a proximal end direction side as the inclined flat surface is away from a first direction (a direction of an arrow A1 shown in FIG. 1 and FIG. 4) toward the second direction. In other words, the inclined flat surface 33 is upwardly inclined from the distal end direction side toward the proximal end direction side of the handle casing 27. In consequence, an angle between the inclined flat surface 33 and the longitudinal axis C is an acute angle β.

As shown in FIG. 1 and FIG. 4, the handle casing 27 has input buttons 35A and 35B that are two operation input portions provided on the inclined flat surface 33. When the input buttons 35A and 35B are pressed, an operator's operation is input. A pressing direction of the input buttons 35A and 35B is perpendicular to, e.g., the inclined flat surface 33.

As shown in FIG. 1 and FIG. 4, the handle casing 27 has switch portions 37A and 37B and an electric circuit substrate 38 provided on an inner peripheral side of the inclined flat surface 33. Opening and closing states of the switch portion 37A are switched by an input operation in the input button 35A. Similarly, opening and closing states of the switch portion 37B are switched by an input operation in the input button 35B.

FIG. 5 is a view schematically showing an electric connection state in the transducer case 11, the cylindrical member 29 and electric connection ring 32. As shown in FIG. 4 and FIG. 5, the handle casing 27 has three electric signal lines, 39A, 39B and 39C provided in the handle casing 27. The electric signal line 39A is electrically connected to the switch portion 37A via the electric circuit substrate 38. The electric signal line 39B is electrically connected to the switch portion 37B via the electric circuit substrate 38. The electric signal line 39C is electrically connected to the switch portion 37A and the switch portion 37B via the electric circuit substrate 38. The electric signal line 39C is a common line to be shared as a ground line of the switch portion 37A and the switch portion 37B.

As shown in FIG. 5, the electric connection ring 32 has a first electric connecting portion 42A, a second electric connecting portion 42B and a third electric connecting portion 42C. The first electric connecting portion 42A is electrically insulated from the second electric connecting portion 42B, the second electric connecting portion 42B is electrically insulated from the third electric connecting portion 42C, and the first electric connecting portion 42A is electrically insulated from the third electric connecting portion 42C. The electric signal line 39A is connected to the first electric connecting portion 42A. The electric signal line 39B is connected to the second electric connecting portion 42B. The electric signal line 39C is connected to the third electric connecting portion 42C.

As shown in FIG. 5, the transducer case 11 has a first conductive portion 43A, a second conductive portion 43B and a third conductive portion 43C. The first conductive portion 43A, the second conductive portion 43B and the third conductive portion 43C are extended along the longitudinal axis C. The first conductive portion 43A is electrically insulated from the second conductive portion 43B, the second conductive portion 43B is electrically insulated from the third conductive portion 43C, and the first conductive portion 43A is electrically insulated from the third conductive portion 43C. In the state where the transducer case 11 is coupled with the fixed handle 22 (the sheath unit 4), a distal end portion of the first conductive portion 43A electrically comes in contact only with the first electric connecting portion 42A. Similarly, a distal end portion of the second conductive portion 43B electrically comes in contact only with the second electric connecting portion 42B. Further, a distal end portion of the third conductive portion 43C electrically comes in contact only with the third electric connecting portion 42C.

As shown in FIG. 5, a proximal end portion of the first conductive portion 43A is connected to one end of an electric signal line 45. A proximal end portion of the second conductive portion 43B is connected to one end of an electric signal line 46. A proximal end portion of the third conductive portion 43C is connected to one end of an electric signal line 47. The electric signal lines 45, 46 and 47 are provided in the cable 6. The other end of each of the electric signal lines 45, 46 and 47 is connected to the power source unit 7.

As described above, a first electric signal path is formed from the switch portion 37A through the electric signal line 39A, the first electric connecting portion 42A, the first conductive portion 43A and the electric signal line 45 to the power source unit 7. A second electric signal path is formed from the switch portion 37B through the electric signal line 39B, the second electric connecting portion 42B, the second conductive portion 43B and the electric signal line 46 to the power source unit 7. Further, a ground path is formed from the switch portion 37A and the switch portion 37B through the electric signal line 39C, the third electric connecting portion 42C, the third conductive portion 43C and the electric signal line 47 to the power source unit 7.

The input button 35A is pressed, thereby bringing the switch portion 37A into a closed state, and the switch portion 37A electrically connects the first electric signal path to the ground path. In consequence, an electric signal is transmitted from the switch portion 37A to the power source unit 7. Further, for example, a current is supplied from the ultrasonic control portion 8 to the ultrasonic transducer 12 via the electric signal lines 13A and 13B. The ultrasonic vibration is generated in the ultrasonic transducer 12, and simultaneously, the state is switched to a state where the high-frequency current is output from the high-frequency current control portion 9.

The input button 35B is pressed, thereby bringing the switch portion 37B into the closed state, and the switch portion 37B electrically connects the second electric signal path to the ground path. In consequence, an electric signal is transmitted from the switch portion 37B to the power source unit 7. Further, for example, a high-frequency current is output only from the high-frequency current control portion 9, and the state is switched to a state where the ultrasonic vibration is not generated.

As shown in FIG. 5, the transducer case 11 further has a fourth conductive portion 43D extended along the longitudinal axis C. Each of the first conductive portion 43A, the second conductive portion 43B and the third conductive portion 43C is electrically insulated from the fourth conductive portion 43D. A proximal end portion of the fourth conductive portion 43D is connected to one end of an electric signal line 48. The electric signal line 48 is provided in the cable 6. The other end of the electric signal line 48 is connected to the high-frequency current control portion 9. In the state where the transducer case 11 is coupled with the fixed handle 22 (the sheath unit 4), only a distal end portion of the fourth conductive portion 43D electrically comes in contact with the cylindrical member 29.

As shown in FIG. 4, the cylindrical member 29 is connected to one end of an electric signal line 49. The other end of the electric signal line 49 is connected to the sheath 23. As described above, the high-frequency current is transmitted from the high-frequency current control portion 9 to the sheath 23 via the electric signal line 48, the fourth conductive portion 43D, the cylindrical member 29, and the electric signal line 49.

Figure 6:
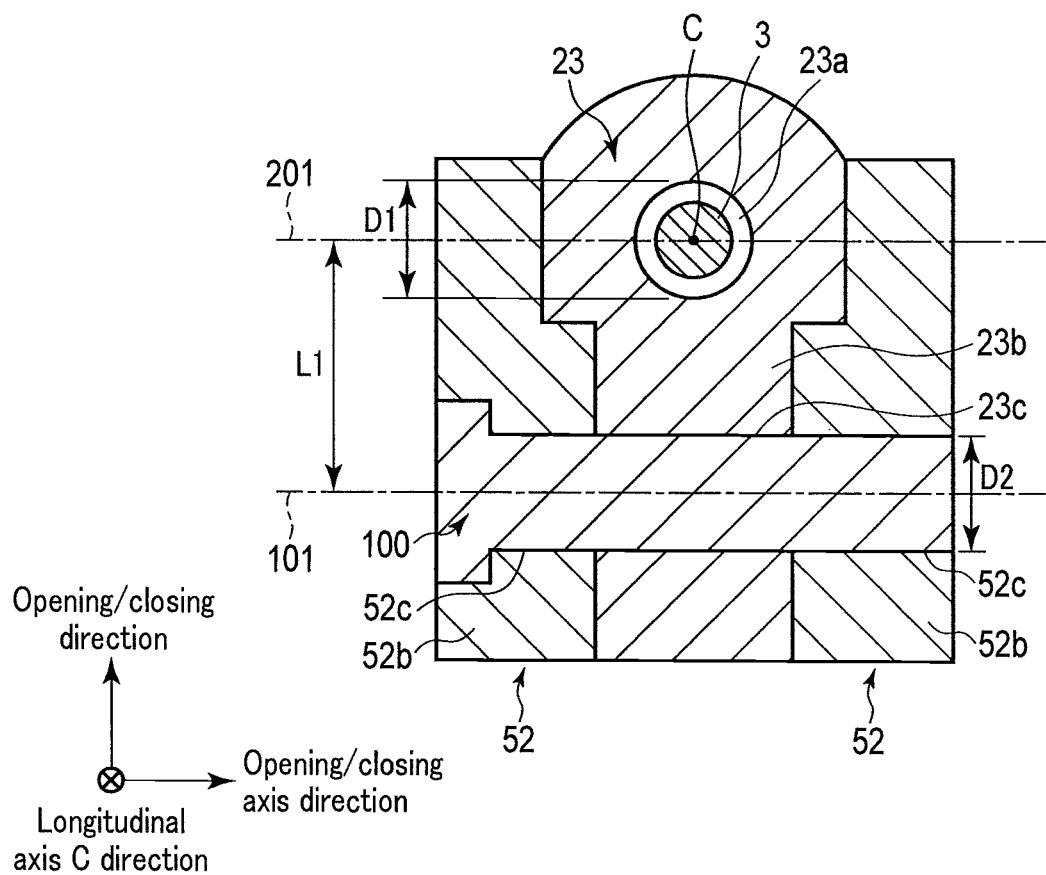
FIG. 6 is a cross-sectional view along the VI-VI line shown in FIG. 1.

As shown in FIG. 6, the sheath 23 is provided on an outer peripheral direction side to the probe 3. The sheath 23 has a hollow portion 23a into which the probe 3 is inserted, in a state where the first electrode portion 21 that functions as the distal end portion of the probe 3 projects from a distal end portion of the sheath 23. The sheath 23 functions as a cylindrical member into which the probe 3 is inserted, and is provided along the longitudinal axis C.

The sheath 23 has an unshown support member that is provided between the probe 3 and the sheath 23 in a radial direction of the sheath 23 to support the probe 3. The support member is made of an insulating material. The support member prevents the probe 3 from coming in contact with the sheath 23, and electrically insulates the probe 3 from the sheath 23. In the present embodiment, the support member is provided at a node position of the ultrasonic vibration. In consequence, the probe 3 is more effectively prevented from coming in contact with the sheath 23. It is to be noted that the number of the support members may be one or plural, as long as at least one support member is provided.

[Movable Handle Unit 5]

As shown in FIG. 1, the movable handle unit 5 is openable and closable on the fixed side including the probe 3 and the sheath unit 4, for a treatment operation to treat the treatment object. The movable handle unit 5 has a movable handle 25 that is provided in a proximal end portion of the movable handle unit and that functions as a power point in the treatment operation. The movable handle 25 is openable and closable in an opening/closing direction to the fixed handle 22 along a periaxial opening/closing direction in an opening/closing axis 101 as a center which will be described later. That is, the movable handle 25 rotates around the opening/closing axis 101. The movable handle 25 has a movable handle ring 26 that functions as a movable side finger placing portion. The movable handle 25 is openable and closable to the fixed handle 22 in the first direction indicating the direction of the arrow A1 of FIG. 1 and perpendicular to the longitudinal axis C and the second direction indicating the direction of the arrow A2 of FIG. 1 and as an opposite direction to the first direction. The movable handle 25 is positioned on the side of the first direction to the fixed handle 22. When the movable handle 25 is closed to the fixed side, a central axis C1 of the movable handle 25 is inclined in a state where the axis has an acute angle α to the longitudinal axis C.

The movable handle unit 5 further has, for example, the jaw 52 rotatably attached to the distal end portion of the sheath 23, and a relay member 57 provided between the movable handle 25 and the jaw 52. The jaw 52 is attached to the sheath 23, thereby coupling the movable handle unit 5 with the sheath unit 4. The jaw 52 has the second electrode portion 53 that is provided in a distal end portion of the movable handle unit 5, functions as an operation point in the treatment operation and functions as a jaw distal end portion. The jaw 52 is attached to the distal end portion of the sheath 23 so that the jaw 52 is rotatable around the opening/closing axis 101, that the opening/closing axis 101 is as the center. The jaw 52 rotates around opening/closing axis 101 as the center with the opening and closing of the movable handle 25, whereby the jaw 52 is openable and closable to the first electrode portion 21 that functions as the distal end portion of the probe 3, in the opening/closing direction which intersect specifically perpendicular to a longitudinal axis direction and an opening/closing axis direction. The jaw 52 including the second electrode portion 53 is openable and closable to the first electrode portion 21. The second electrode portion 53 is positioned on the side of the second direction (the direction of the arrow A2 shown in FIG. 1) to the first electrode portion 21. The second electrode portion 53 is electrically connected to the sheath 23. The second electrode portion 53 has a probe facing portion 55 that is provided in a part on an outer surface of the second electrode portion 53 (the jaw 52) and on the side of the first direction (the direction of the arrow A1 shown in FIG. 1) and that faces the first electrode portion 21. Similarly, the first electrode portion 21 has a jaw facing portion 58 that is provided in a part on an outer surface of the first electrode portion 21 and on the side of the second direction (the direction of the arrow A2 shown in FIG. 1) and that faces the second electrode portion 53.

Consequently, the movable handle 25 moves in the first direction, and the movable handle 25 performs an opening operation to the fixed handle 22, whereby the jaw 52 including the second electrode portion 53 moves in the second direction. In consequence, the jaw 52 including the second electrode portion 53 is at an opening position to the first electrode portion 21.

The movable handle 25 moves in the second direction, and the movable handle 25 performs a closing operation to the fixed handle 22, whereby the jaw 52 including the second electrode portion 53 moves in the first direction. In consequence, the jaw 52 including the second electrode portion 53 is at a closing position to the first electrode portion 21.

That is, when the jaw 52 rotates around the opening/closing axis 101 as the center to the sheath 23, the jaw 52 performs the opening/closing operation at the opening position and the closing position to the first electrode portion 21. In this way, the movable handle 25 performs the opening/closing operation of the jaw 52, and is openable and closable to the fixed handle 22.

As described above, the second electrode portion 53 is electrically connected to the sheath 23. Thus, the high-frequency current is transmitted between the sheath 23 and the second electrode portion 53. The high-frequency current is transmitted between the high-frequency current control portion 9 and the sheath 23 via the electric signal line 48, the fourth conductive portion 43D and the electric signal line 49. Therefore, a jaw side current path is formed from the high-frequency current control portion 9 through the electric signal line 48, the fourth conductive portion 43D, the electric signal line 49 and the sheath 23 to the second electrode portion 53 of the jaw 52. The jaw side current path indicates a path through which the high-frequency current flows. That is, the high-frequency current is transmitted between the high-frequency current control portion 9 and the second electrode portion 53 by the jaw side current path.

It is to be noted that an outer surface of the sheath 23 and the outer surface of a portion of the jaw 52 other than the probe facing portion 55 are treated with, e.g., an insulating coating. Consequently, even in a case where an operator's hand or the like comes in contact with the outer surface of the sheath 23 or the outer surface of the jaw 52, an electric shock is prevented from being received. The relay member 57 between the jaw 52 and the movable handle 25 is made of an insulating material. In consequence, the high-frequency current is prevented from being transmitted from the jaw 52 to the movable handle 25.

[Opening/Closing Axis Member 100]

As shown in FIG. 1 and FIG. 6, the treatment device 10 further has an opening/closing axis member 100 that has the opening/closing axis 101 and that attaches the jaw 52 to the sheath 23 so that the jaw 52 rotates around the opening/closing axis, whereby the jaw 52 is openable and closable to the sheath 23. The opening/closing axis 101 corresponds to a central axis of the opening/closing axis member 100. The opening/closing axis member 100 including the opening/closing axis 101 may be included in the movable handle unit 5 of the treatment device 10.

As shown in FIG. 1 and FIG. 6, an axis that is provided along a perpendicular direction perpendicular to opening/closing directions such as the first direction (the direction of the arrow A1 shown in FIG. 1) and the second direction (the direction of the arrow A2 shown in FIG. 1) and a longitudinal axis C direction and that is perpendicular to the longitudinal axis C is defined as a perpendicular axis 201. The perpendicular direction is the opening/closing axis direction shown in FIG. 6. The perpendicular axis 201 is provided along a radial direction of the probe 3 and the radial direction of the sheath 23. The perpendicular axis 201 intersects the longitudinal axis C and extends through the hollow portion 23a.

As shown in FIG. 1, the perpendicular axis 201 is provided more forward than, e.g., an intersecting axis 301 in the longitudinal axis C direction. A forward side here refers to the side of the first electrode portion 21 that functions as the distal end portion of the probe 3 in the longitudinal axis C direction. Similarly to the perpendicular axis 201, the intersecting axis 301 is an axis that is provided along the opening/closing axis direction perpendicular to the opening/closing direction and the longitudinal axis C direction and that is perpendicular to the longitudinal axis C. The intersecting axis 301 intersects the central axis C1 of the movable handle 25.

As shown in FIG. 1 and FIG. 6, the opening/closing axis 101 of the present embodiment is provided to shift from the intersecting axis 301 in the longitudinal axis C direction. For example, the opening/closing axis 101 is provided more forward than the intersecting axis 301 in the longitudinal axis C direction. Further, the opening/closing axis 101 is not provided on the perpendicular axis 201. The opening/closing axis 101 is provided to shift from the perpendicular axis 201 in the opening/closing direction. Specifically, the opening/closing axis 101 is away from the perpendicular axis 201 in the opening/closing direction, and is provided in parallel with the perpendicular axis 201 in the opening/closing axis direction. In other words, the opening/closing axis 101 is offset to the perpendicular axis 201 in the opening/closing direction. The opening/closing axis 101 is provided on the side of the second direction to the perpendicular axis 201. Thus, the opening/closing axis 101 does not intersect the perpendicular axis 201, and does not penetrate the hollow portion 23a.

As shown in FIG. 6, the opening/closing axis member 100 is provided at a position offset to the hollow portion 23a in the opening/closing direction so that the opening/closing axis member 100 does not overlap with the hollow portion 23a in the opening/closing direction. In this state, the opening/closing axis member 100 having the opening/closing axis 101 is inserted in the jaw 52 and the sheath 23 so that the opening/closing axis member 100 pierces through (skewers) the sheath 23 and the jaw 52 provided adjacent to each other in the opening/closing axis direction at a position at which the opening/closing axis member 100 is offset to the hollow portion 23a in the opening/closing direction. The opening/closing axis member 100 is inserted in, whereby the opening/closing axis member 100 attaches the jaw 52 to the sheath 23.

As shown in FIG. 6, the treatment device 10 further has a sheath side attaching portion 23b that is provided in the sheath 23, and a jaw side attaching portion 52b that is provided in the jaw 52. The sheath side attaching portion 23b and the jaw side attaching portion 52b are provided so that one opening/closing axis member 100 pierces through the sheath side attaching portion 23b and the jaw side attaching portion 52b in the opening/closing axis direction at the position offset to the hollow portion 23a in the opening/closing direction. Consequently, the sheath side attaching portion 23b and the jaw side attaching portion 52b are provided at the positions offset to the hollow portion 23a in the opening/closing direction, and are adjacent to each other and further overlapped with each other in the opening/closing axis direction. Consequently, as shown in FIG. 1, the opening/closing axis member 100 including the opening/closing axis 101, the sheath side attaching portion 23b and the jaw side attaching portion 52b are provided closer to, e.g., a fixed handle 22 side than to a movable handle 25 side in the opening/closing direction. These positions will be described later in detail.

As shown in FIG. 6, the sheath side attaching portion 23b has a sheath side through hole portion 23c that penetrates the sheath side attaching portion 23b in the opening/closing axis direction and is provided away from the hollow portion 23a in the opening/closing axis direction and the opening/closing direction.

As shown in FIG. 6, the jaw side attaching portion 52b has a jaw side through hole portion 52c that penetrates the jaw side attaching portion 52b in the opening/closing axis direction and is provided away from the hollow portion 23a in the opening/closing axis direction and the opening/closing direction.

As shown in FIG. 6, in the present embodiment, when the jaw 52 is attached to the sheath 23, the one opening/closing axis member 100 is inserted in the sheath side through hole portion 23c and the jaw side through hole portion 52c in a state where the jaw side through hole portion 52c communicates with the sheath side through hole portion 23c in the opening/closing axis direction. The one opening/closing axis member 100 attaches the jaw 52 to the sheath 23 so that the jaw 52 is made openable and closable to the sheath 23 by inserting the one opening/closing axis member 100 in the sheath side through hole portion 23c and the jaw side through hole portion 52c. In the opening/closing axis direction, each end face of the opening/closing axis member 100 is provided on the same flat surface as the outer peripheral surface of the jaw side attaching portion 52b. That is, in the opening/closing axis direction, both end portions of the opening/closing axis member 100 do not project from the jaw side attaching portion 52b. In the present embodiment, the opening/closing axis member 100 is only inserted in the sheath side through hole portion 23c and the jaw side through hole portion 52c.

Here, as shown in FIG. 6, a diameter of the hollow portion 23a of the sheath 23 is defined as D1, a diameter of the sheath side through hole portion 23c is defined as D2, a distance between a central position of the hollow portion 23a and the sheath side through hole portion 23c in the opening/closing direction is defined as L1, the offset is taken into consideration in the above definitions, and then Equation (1) is established as follows:

$$(D1+D2)/2 < L1 \qquad \text{Equation (1).}$$

In the above description, L1 corresponds to a distance between the perpendicular axis 201 and the opening/closing axis 101 in the opening/closing direction.

According to Equation (1), the sheath side through hole portion 23c, the jaw side through hole portion 52c and the opening/closing axis member 100 are securely offset to the hollow portion 23a in the opening/closing direction. As shown in FIG. 6, the opening/closing axis member 100 including the opening/closing axis 101 is not provided on the perpendicular axis 201, and is not inserted in the hollow portion 23a.

The opening/closing axis member 100 is not fixed to, e.g., both of the sheath side attaching portion 23b and the jaw side attaching portion 52b, or is fixed to one of the sheath side attaching portion 23b and the jaw side attaching portion 52b. That is, the opening/closing axis member 100 is not fixed to at least one of the sheath side attaching portion 23b and the jaw side attaching portion 52b.

In a case where the opening/closing axis member 100 is not fixed to both of the sheath side attaching portion 23b and the jaw side attaching portion 52b, the jaw side attaching portion 52b and the jaw 52 are rotatable to the opening/closing axis member 100, the sheath side attaching portion 23b and the sheath 23 around the opening/closing axis.

In a case where the opening/closing axis member 100 is fixed to the sheath side attaching portion 23b and is not fixed to the jaw side attaching portion 52b, the jaw side attaching portion 52b and the jaw 52 are rotatable to the opening/closing axis member 100, the sheath side attaching portion 23b and the sheath 23 around the opening/closing axis.

In a case where the opening/closing axis member 100 is not fixed to the sheath side attaching portion 23b and is fixed to the jaw side attaching portion 52b, the jaw side attaching portion 52b, the jaw 52 and the opening/closing axis member 100 are integrally rotatable to the sheath side attaching portion 23b and the sheath 23 around the opening/closing axis.

As described above and as shown in FIG. 1 and FIG. 6, the jaw 52 is attached to the sheath 23 by the one opening/closing axis member 100 so that the jaw 52 is rotatable by the sheath side attaching portion 23b, the jaw side attaching portion 52b and the one opening/closing axis member 100 around the opening/closing axis.

In this way, the opening/closing axis member 100 having the opening/closing axis 101, the sheath side attaching portion 23b having the sheath side through hole portion 23c and the jaw side attaching portion 52b having the jaw side through hole portion 52c function as attaching portions that attach the jaw 52 to the sheath 23. This attaching portion attaches the movable handle unit 5 to the fixed side so that the movable handle unit 5 is rotatable around the opening/closing axis.

This attaching portion functions as an electric contact unit that is provided between the sheath 23 and the jaw 52, and that holds a state where the high-frequency current is always transmitted between the sheath 23 and the second electrode portion of the jaw 52. In the opening/closing axis member 100 inserted in the sheath side through hole portion 23c and the jaw side through hole portion 52c, for example, the outer peripheral surface of the opening/closing axis member 100 comes in contact with the inner peripheral surface of the sheath side attaching portion 23b and the inner peripheral surface of the jaw side attaching portion 52b, whereby the high-frequency current is transmitted between the sheath 23 and the second electrode portion of the jaw 52.

It is to be noted that an exposed portion of the opening/closing axis member 100 which is exposed out from the sheath side attaching portion 23b and the jaw side attaching portion 52b, an outer surface of the sheath side attaching portion 23b and an outer surface of the jaw side attaching portion 52b are subjected to, e.g., an insulating coating treatment. Consequently, even in a case where the operator's hand or the like comes in contact with these parts, an electric shock is prevented from being received.

[Sheath Side Attaching Portion 23b]

As shown in FIG. 6, as one example of a position of the sheath side attaching portion 23b, the sheath side attaching portion 23b is provided on the same axis as in, e.g., the hollow portion 23a of the sheath 23 into which the probe 3 is inserted, in the opening/closing direction. The sheath side attaching portion 23b is provided on, e.g., a lower side of the hollow portion 23a in the opening/closing direction. In this case, the sheath side attaching portion 23b is formed by, e.g., a thick portion of the sheath 23 that extends from the longitudinal axis C toward the second direction in the opening/closing direction. In this way, the sheath side attaching portion 23b is provided on the fixed handle 22 side in the opening/closing direction. The sheath side attaching portion 23b is preferably provided in, e.g., a part of the distal end portion of the sheath 23. In this way, the sheath side attaching portion 23b of the present embodiment is, e.g., a part of the sheath 23 and is integral with the sheath 23.

As shown in FIG. 6 and as described above, the sheath side through hole portion 23c does not communicate with the hollow portion 23a, and is separated from the hollow portion 23a in the opening/closing axis direction and the opening/closing direction. The sheath side through hole portion 23c is provided to be offset so that the sheath side through hole portion 23c does not overlap with the hollow portion 23a in the opening/closing direction. In this way, the thick portion of the sheath side attaching portion 23b is interposed between the hollow portion 23a and the sheath side through hole portion 23c. The sheath side through hole portion 23c is provided on, e.g., the lower side of the hollow portion 23a in the opening/closing direction, and provided closer to, e.g., the fixed handle 22 side than to the movable handle 25 side.

[Jaw Side Attaching Portion 52b]

As shown in FIG. 6, the jaw side attaching portion 52b is a part of the jaw 52, and a pair of jaw side attaching portions are provided. The jaw side attaching portions 52b are provided on both sides of the sheath side attaching portion 23b to sandwich the sheath side attaching portion 23b therebetween in the opening/closing axis direction. Specifically, the jaw side attaching portions 52b sandwich a pair of side surface portions provided on both the sides of the sheath side attaching portion 23b in the opening/closing axis direction. The jaw side attaching portions 52b sandwich the sheath side attaching portion 23b therebetween so that the jaw side through hole portion 52c communicates with the sheath side through hole portion 23c in the opening/closing axis direction. For example, the jaw side attaching portions 52b are formed by providing a through hole portion 59 (see FIG. 9A) in the jaw 52 which will be described later. The jaw side attaching portions 52b function as a pair of arm portions of the jaw 52 which are formed by providing the through hole portion 59. In other words, the jaw 52 is divided into two sections by the through hole portion 59. The through hole portion 59 penetrates the jaw 52 in the longitudinal axis C direction. The through hole portion 59 is interposed between the jaw side attaching portions 52b in the opening/closing axis direction. The sheath 23 is insertable into the through hole portion 59.

As shown in FIG. 6 and as described above, similarly to the sheath side through hole portion 23c, the jaw side through hole portion 52c does not communicate with the hollow portion 23a, and is separated from the hollow portion 23a in the opening/closing axis direction and the opening/closing direction. The sheath side through hole portion 23c is provided to be offset so that the sheath side through hole portion does not overlap with the hollow portion 23a in the opening/closing direction. In this way, between the hollow portion 23a and the jaw side through hole portion 52c, there are interposed the thick portion of the sheath side attaching portion 23b, a thick portion of the jaw side attaching portion 52b, and a thick portion of the sheath 23. The jaw side through hole portion 52c is provided on, e.g., the lower side than the hollow portion 23a, and provided closer to, e.g., the fixed handle 22 side than to the movable handle 25 side in the opening/closing direction.

[Operation]

As shown in FIG. 6, the jaw side attaching portions 52b sandwich the sheath side attaching portion 23b so that the jaw side through hole portion 52c communicates with the sheath side through hole portion 23c in the opening/closing axis direction. At this time, the sheath side through hole portion 23c and the jaw side through hole portion 52c are provided at positions offset to the hollow portion 23a in the opening/closing direction and provided, e.g., adjacent to each other in the opening/closing axis direction.

In this state, as shown in FIG. 6, the sheath side through hole portion 23c and the jaw side through hole portion 52c do not communicate with the hollow portion 23a in the opening/closing axis direction and the opening/closing direction, and are offset to the hollow portion 23a so that the through hole portions do not overlap with the hollow portion 23a in the opening/closing direction.

As shown in FIG. 6, the one opening/closing axis member 100 is inserted in the sheath side through hole portion 23c and the jaw side through hole portion 52c so that the one opening/closing axis member 100 pierces through (skewers) the sheath side attaching portion 23b and the jaw side attaching portion 52b.

Consequently, as shown in FIG. 6, the one opening/closing axis member 100 is not provided on the perpendicular axis 201, and is provided at the position offset to the hollow portion 23a in the opening/closing direction. The one opening/closing axis member 100 attaches the jaw 52 to the sheath 23 at the offset position. The one opening/closing axis member 100 is not inserted in the hollow portion 23a.

As shown in FIG. 6 and as described above, the jaw 52 does not communicate with the hollow portion 23a in the opening/closing axis direction and the opening/closing direction, and the jaw 52 is attached to the sheath 23 by the one opening/closing axis member 100 at the position offset to the hollow portion 23a in the opening/closing direction. At this time, the jaw 52 is attached to the sheath 23 by the one opening/closing axis member 100, to be rotatable around the opening/closing axis.

[Effect]

Consequently, in the present embodiment, the one opening/closing axis member 100 is provided at the position offset to the hollow portion 23a in the opening/closing direction. At this time, the one opening/closing axis member 100 does not overlap with the hollow portion 23a and does not penetrate the hollow portion 23a. The one opening/closing axis member 100 attaches the jaw 52 to the sheath 23 at the offset position.

In the present embodiment, a pair of opening/closing axis members 100 are not provided, i.e., it does not follow that one opening/closing axis member 100 is inserted in the sheath side through hole portion 23c and one jaw side through hole portion 52c and that the other opening/closing axis member 100 is inserted in the sheath side through hole portion 23c and the other jaw side through hole portion 52c. In the present embodiment, the opening/closing axis member 100 pierces through the sheath side attaching portion 23b and the jaw side attaching portion 52b so that the one opening/closing axis member 100 is inserted in the one jaw side through hole portion 52c, the sheath side attaching portion 23b and the other jaw side through hole portion 52c.

Therefore, in the present embodiment, the number of components for the attaching can be minimized, and the opening/closing axis 101 can highly accurately be provided. In the present embodiment, an attaching configuration can be simplified, and generation of looseness in the attaching portion between the jaw 52 and the sheath 23 can be prevented. In the present embodiment, even when a shape error of a product itself is large, the generation of the looseness in the attaching portion between the jaw 52 and the sheath 23 can be prevented.

In the present embodiment, as described above, a relative position between the distal end portion of the probe 3 and the distal end portion of the jaw 52 can be prevented from shifting, and in this state, a meshing accuracy can be prevented from being deteriorated in meshing of the distal end portion of the probe 3 and the distal end portion of the jaw 52 with each other. Therefore, according to the present embodiment, in treatment operations such as a grasping operation and a peeling operation, treatment forces such as a grasping force and a peeling force can be prevented from being deteriorated, and desirable treatment characteristics can securely be obtained.

In the present embodiment, it is possible to obtain an operation feeling of the treatment device 10 similar to that of the treatment device 10 of such a type that the opening/closing axis 101 crosses the longitudinal axis C similarly to the perpendicular axis 201. In other words, according to the present embodiment, the opening/closing axis 101 is offset, but it is possible to obtain the operation feeling that is not different from that in a conventional treatment device.

In the present embodiment, when the jaw 52 is attached to the sheath 23, the sheath side through hole portion 23c and the jaw side through hole portion 52c communicate with each other. Therefore, in the present embodiment, the opening/closing axis member 100 can easily be inserted into and pulled out from the sheath 23 and the jaw 52, and attaching and detaching can easily be performed.

In the present embodiment, the offset can securely be performed by (D1+D2)/2<L1. In the present embodiment, by (D1+D2)/2<L1, a body fluid or the like that has permeated into the hollow portion 23a during the treatment operation can securely be prevented from leaking to the outside of the treatment device 10 via the sheath side through hole portion 23c and the jaw side through hole portion 52c.

In the present embodiment, the opening/closing axis member 100 is inserted in the sheath side attaching portion 23b as a part of the sheath 23 and the jaw side attaching portion 52b as a part of the jaw 52. Consequently, in the present embodiment, for the attaching, the opening/closing axis member 100, the sheath side through hole portion 23c and the jaw side through hole portion 52c need only be prepared. Therefore, in the present embodiment, the number of the components for the attaching can be decreased.

It is to be noted that in the present embodiment, as shown in FIG. 6, the sheath side through hole portion 23c is provided on, e.g., the lower side of the hollow portion 23a in the opening/closing direction, and provided on the fixed handle 22 side. The opening/closing axis member 100 having the opening/closing axis 101 and the jaw side through hole portion 52c are provided on, e.g., the side lower than the hollow portion 23a and provided closer to, e.g., the fixed handle 22 side than to the movable handle 25 side in the opening/closing direction. In other words, the opening/closing axis member 100, the sheath side through hole portion 23c and the jaw side through hole portion 52c are provided between, e.g., the hollow portion 23a including the longitudinal axis C and the fixed handle ring 28 in the opening/closing direction. However, when the opening/closing axis member 100, the sheath side through hole portion 23c and the jaw side through hole portion 52c are provided at the positions offset to the hollow portion 23a in the opening/closing direction, these positions do not have to be limited to those in this example.

Figure 7A:
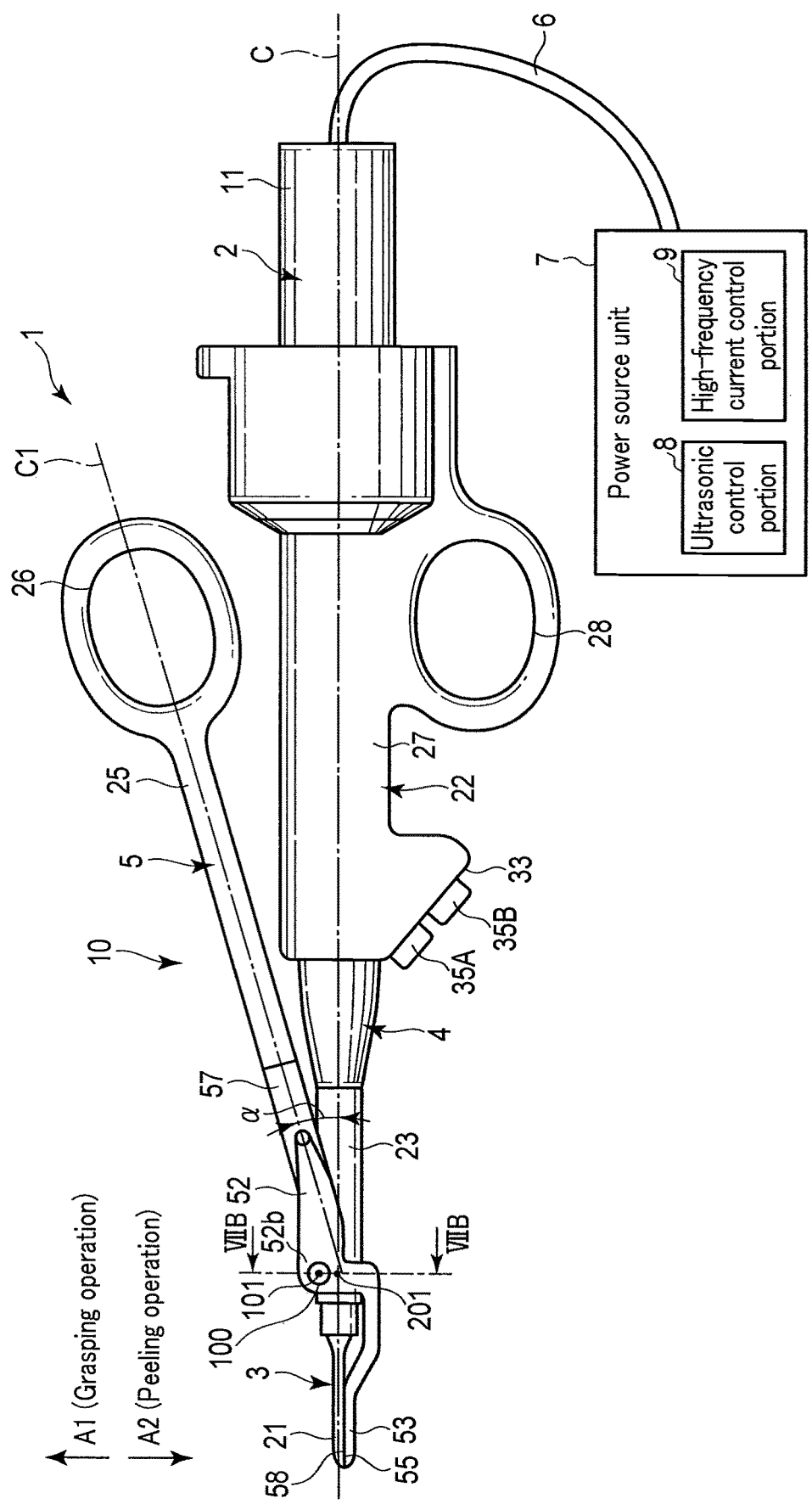
FIG. 7A is a schematic view of a medical treatment apparatus showing one example of an arrangement of an attaching portion of the present invention.
Figure 7B:
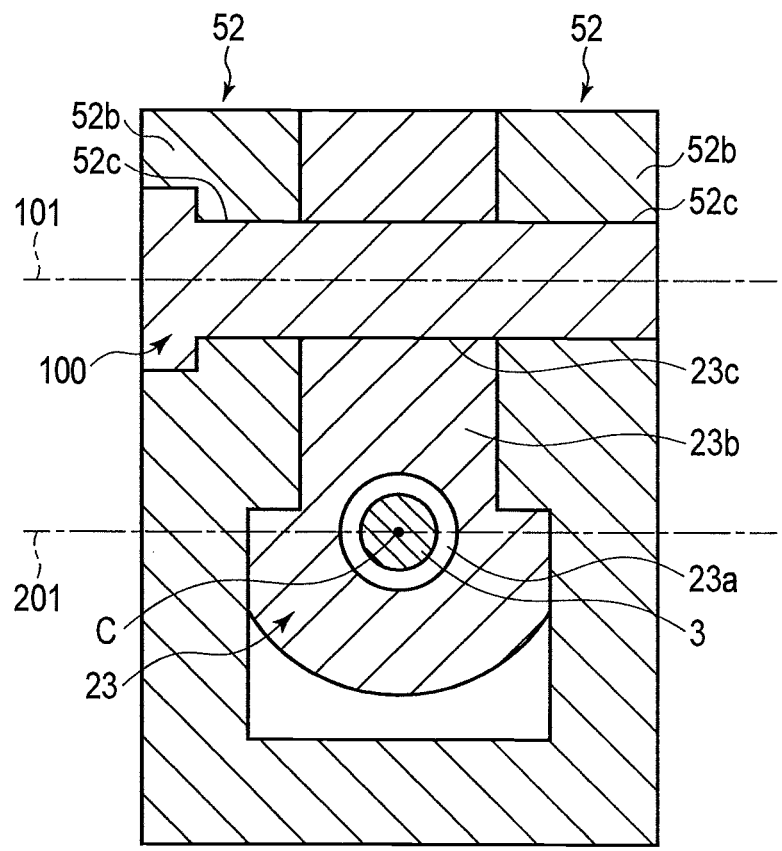
FIG. 7B is a cross-sectional view along the VIIB-VIIB line shown in FIG. 7A.
Figure 7B:
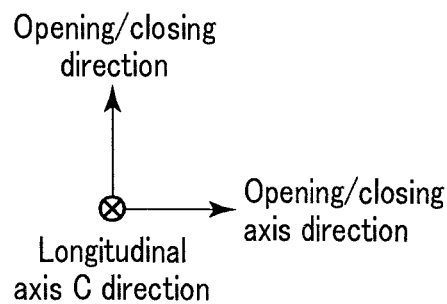

For example, as shown in FIG. 7A and FIG. 7B, the sheath side attaching portion 23b may be provided on, e.g., a side higher than the hollow portion 23a and provided closer to, e.g., the movable handle 25 side than to the fixed handle 22 side in the opening/closing direction. In consequence, the sheath side through hole portion 23c is provided on, e.g., the side higher than the hollow portion 23a and provided closer to, e.g., the movable handle 25 side than to the fixed handle 22 side. The opening/closing axis member 100 and the jaw side through hole portion 52c are provided on, e.g., the higher side than the hollow portion 23a and provided closer to, e.g., the movable handle 25 side than to the fixed handle 22 side in the opening/closing direction. In other words, the opening/closing axis member 100, the sheath side through hole portion 23c and the jaw side through hole portion 52c are provided between, e.g., the hollow portion 23a including the longitudinal axis C and the movable handle 25 in the opening/closing direction.

In the present embodiment, the opening/closing axis 101 is provided more forward than the intersecting axis 301 in the longitudinal axis C direction, but the present invention does not have to be limited to this example. There is no special restriction on an axial position of the opening/closing axis 101 to the intersecting axis 301 in the longitudinal axis C direction.

In the present embodiment, the sheath side attaching portion 23b is integral with the sheath 23, but the present invention does not have to be limited to this example. The sheath side attaching portion 23b may be a separate member from the sheath 23. In this case, the sheath side attaching portion 23b may be attached to the outer peripheral surface of the distal end portion of the sheath 23 by, e.g., adhesive bonding, welding or the like.

In the present embodiment, the jaw side attaching portions 52b sandwich the sheath side attaching portion 23b therebetween, but the present invention is not limited to this example. For example, the sheath side attaching portions 23b may sandwich the jaw side attaching portion 52b therebetween. Thus, in the opening/closing axis direction, one of the sheath side attaching portion 23b and the jaw side attaching portion 52b may sandwich the other portion so that the sheath side through hole portion 23c communicates with the jaw side through hole portion 52c and the sheath side attaching portion 23b and the jaw side attaching portion 52b are superimposed on each other.

In the present embodiment, when the opening/closing axis member 100 is provided so that the opening/closing axis member 100 pierces into the sheath side attaching portion 23b and the jaw side attaching portion 52b, a configuration of the sheath side attaching portion 23b and the jaw side attaching portion 52b does not have to be limited to the abovementioned sandwiching configuration. For example, the sheath side attaching portion 23b and the jaw side attaching portion 52b may be provided in parallel with each other in the opening/closing axis direction, as long as the opening/closing axis member 100 is provided so that the opening/closing axis member 100 pierces through the sheath side attaching portion 23b and the jaw side attaching portion 52b. That is, in the opening/closing axis direction, an unshown member may be interposed between the sheath side attaching portion 23b and the jaw side attaching portion 52b, or the sheath side attaching portion 23b and the jaw side attaching portion 52b may be provided away from each other. In the opening/closing axis direction, the sheath side attaching portion 23b may be sandwiched between the jaw side attaching portions 52b, may be interposed between the jaw side attaching portions 52b, may come in contact closely with the jaw side attaching portions 52b, or may be separated from the jaw side attaching portions 52b.

Figure 8A:
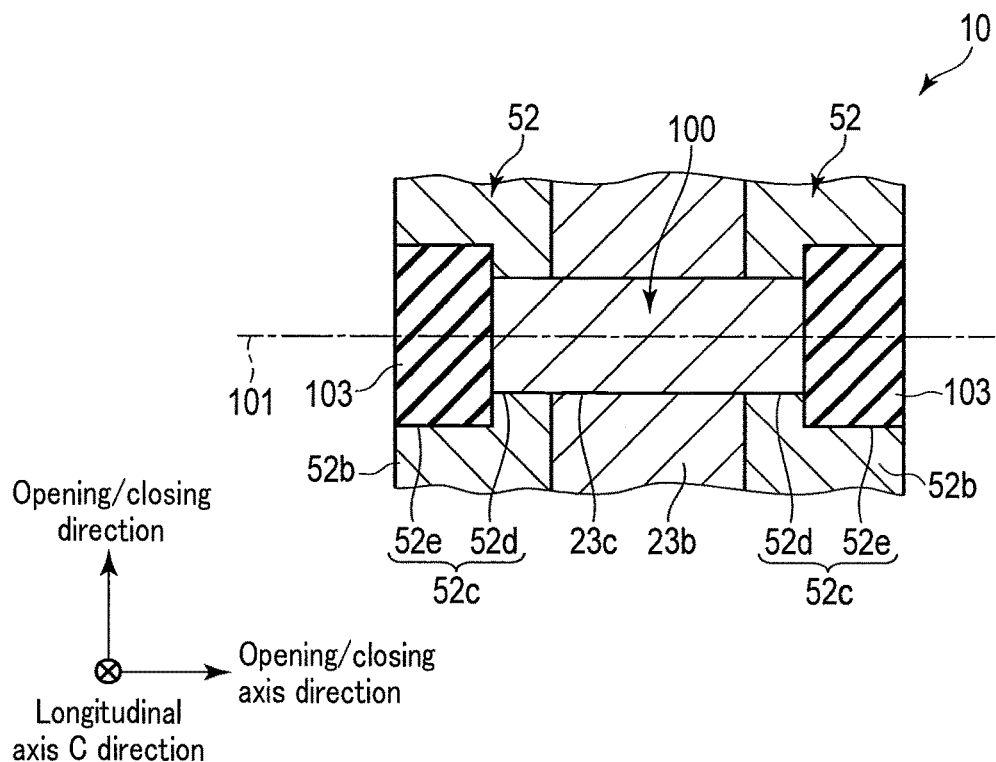
FIG. 8A is a cross-sectional view along the VI-VI line shown in FIG. 1, and a view showing one example of an arrangement of preventing members.

As shown in FIG. 8A, the treatment device 10 may further have preventing members 103 that prevent the opening/closing axis member 100 from falling out from the sheath side through hole portion 23c and the jaw side through hole portion 52c. The preventing members 103 are fitted into, e.g., the respective jaw side through hole portions 52c. In this case, a pair of preventing members 103 sandwich the opening/closing axis member 100 therebetween in the opening/closing axis direction. The preventing members 103 are separate members from each other.

As shown in FIG. 8A, the opening/closing axis member 100 is inserted in the sheath side through hole portion 23c and the jaw side through hole portion 52c, and further, the preventing members 103 are fitted into the jaw side through hole portions 52c. In the opening/closing axis direction, the preventing members 103 are provided on the same flat surface as the outer peripheral surfaces of the jaw side attaching portions 52b. That is, in the opening/closing axis direction, the preventing members 103 do not project from the jaw side attaching portions 52b.

The opening/closing axis member 100 is an axial member, and the preventing member 103 is a rod member thicker than the opening/closing axis member 100 and functions as a cap.

As shown in FIG. 8A, the jaw side through hole portion 52c has a convex shape, and has a first hole portion 52d in which the opening/closing axis member 100 is inserted, and a second hole portion 52e in which the preventing member 103 is inserted. In the opening/closing axis direction, the first hole portion 52d communicates with the second hole portion 52e and the sheath side through hole portion 23c. A diameter of the first hole portion 52d is the same as a diameter of the opening/closing axis member 100 and the diameter of the sheath side through hole portion 23c, and smaller than a diameter of the preventing member 103 and a diameter of the second hole portion 52e. The diameter of the second hole portion 52e is the same as the diameter of the preventing member 103. In the opening/closing axis direction, the second hole portion 52e is provided on an outer side of the first hole portion 52d.

As shown in FIG. 8A, the preventing members 103 are fitted into the jaw side through hole portions 52c, and hence the opening/closing axis member 100 can be prevented from falling out from the sheath side through hole portion 23c and the jaw side through hole portion 52c by the preventing members 103.

It is to be noted that the opening/closing axis member 100 is made of, e.g., a hard material. This material is, for example, a metal or a resin.

In a case where the opening/closing axis member 100 is made of, e.g., a conductive material, the preventing members 103 may be made of an insulating material. In this case, the preventing members 103 are made of a rubber, a ceramic material, a hard resin or the like. In consequence, even when the high-frequency current flows through the jaw 52, the high-frequency current can be prevented from flowing outside via the opening/closing axis member 100.

Figure 8B:
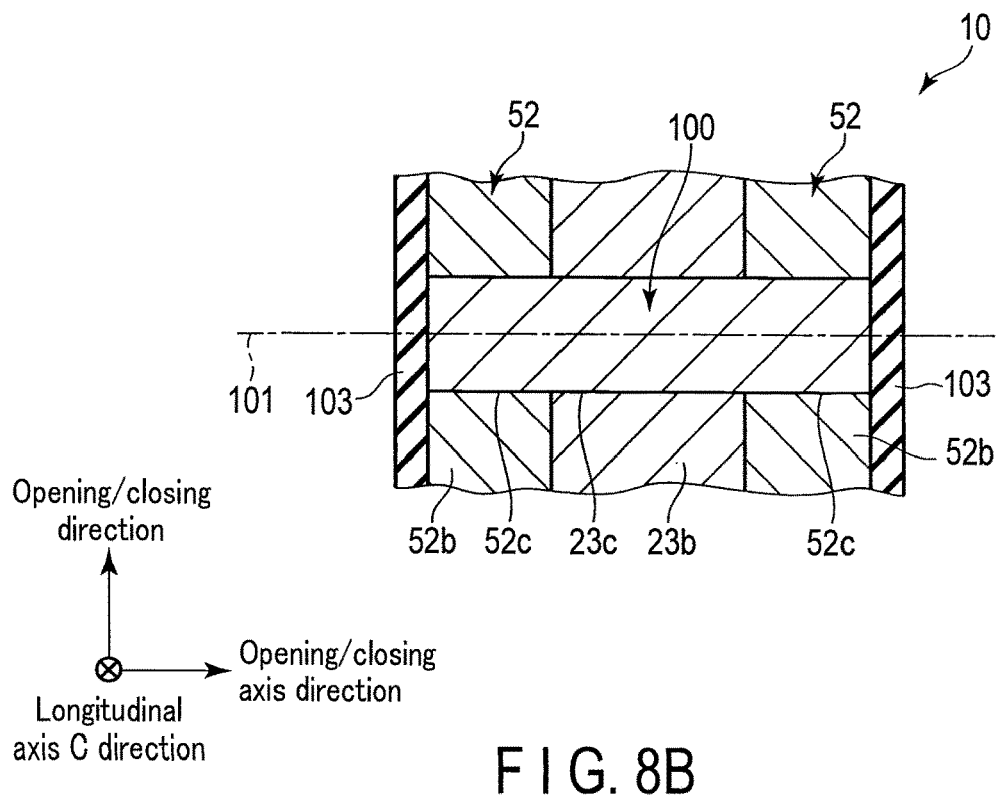
FIG. 8B is a cross-sectional view along the VI-VI line shown in FIG. 1, and a view showing one example of the arrangement of the preventing members.

As shown in FIG. 8B, the preventing members 103 may cover the outer peripheral surfaces of the jaw side attaching portions 52b including end faces of the opening/closing axis member 100.

As shown in FIG. 8A and FIG. 8B, an outer diameter of the opening/closing axis member 100 is uniform, but the present invention is not limited to this example. As shown in FIG. 6, the outer diameter of the opening/closing axis member 100 may change so that the opening/closing axis member 100 has stepped portions. The shape of the jaw side through hole portion 52c may be suitably changed in accordance with a shape of the opening/closing axis member 100.

Second Embodiment

[Configuration]
Only aspects that differ from the first embodiment will be described next, with reference to FIG. 9A, FIG. 9B and FIG. 9C. The present embodiment corresponds to a configuration shown in FIG. 1 and FIG. 6.

As shown in FIG. 9A, FIG. 9B and FIG. 9C, a treatment device 10 further has a regulating mechanism 150 that regulates an opening/closing angle of a jaw 52 to a sheath 23.

The regulating mechanism 150 has the sheath 23 into which a through hole portion 59 to be provided in the jaw 52 is inserted, and a projecting portion 151 provided on an outer peripheral surface of the sheath 23 to project toward an outer side of the sheath 23 in a radial direction of the sheath 23. The regulating mechanism 150 further has an inner peripheral surface 59a of the through hole portion 59 which abuts on the outer peripheral surface of the sheath 23 when a movable handle unit 5 including the jaw 52 closes to a fixed side as shown in FIG. 9B, and which abuts on the projecting portion 151 when the movable handle unit 5 including the jaw 52 opens to the fixed side as shown in FIG. 9C.

As shown in FIG. 9B and FIG. 9C, the projecting portion 151 is provided on the side of a first direction. Specifically, the projecting portion 151 is provided on an upper surface of the sheath 23 which faces the movable handle unit 5. The projecting portion 151 is provided on the side opposite to an opening/closing axis member 100 via the sheath 23 in an opening/closing direction. The projecting portion 151 is formed by projecting a part of the sheath 23 toward the outer side of the sheath 23 in the radial direction of the sheath 23. Thus, the projecting portion 151 is integral with the sheath 23. It is to be noted that the projecting portion 151 may be a separate body from the sheath 23.

As shown in FIG. 9B and FIG. 9C, in the through hole portion 59 including the inner peripheral surface 59a, a relative position of the through hole portion 59 to the projecting portion 151 and the sheath 23 changes in accordance with an opening/closing operation of the movable handle unit 5.

As shown in FIG. 9B and FIG. 9C, the inner peripheral surface 59a of the through hole portion 59 has a first abutment region 59b that abuts on the outer peripheral surface of the sheath 23 so that a probe facing portion 55 abuts on a jaw facing portion 58 when the movable handle unit 5 closes to the fixed side, and a second abutment region 59c that abuts on the projecting portion 151 when the movable handle unit 5 opens to the fixed side.

As shown in FIG. 9B and FIG. 9C, the first abutment region 59b and the second abutment region 59c are provided on the side opposite to the opening/closing axis member 100 via the sheath 23 in the opening/closing direction. The first abutment region 59b is provided on a lower surface side of the jaw 52, and the second abutment region 59c is provided on an upper surface side of the jaw 52. This lower surface of the jaw 52 is a surface reverse to the upper surface of the jaw 52, and faces the sheath 23. The first abutment region 59b and the second abutment region 59c are provided in a proximal end portion of the through hole portion 59. The first abutment region 59b includes an inner peripheral edge portion on the lower surface side of the jaw 52, and the second abutment region 59c includes an inner peripheral edge portion on the upper surface side of the jaw 52. The outer peripheral surface of the sheath 23 on which the first abutment region 59b abuts is an upper surface portion of the sheath 23 which faces the movable handle unit 5. The outer peripheral surface of the sheath 23 on which the first abutment region 59b abuts is provided on the same straight line as that of the projecting portion 151 in a longitudinal axis C direction. As shown in FIG. 9B, in a state where the movable handle unit 5 is closed, the inner peripheral surface 59a is inclined in the longitudinal axis C direction so that the second abutment region 59c is positioned more forward than the first abutment region 59b.

[Operation]

As shown in FIG. 9B, when the movable handle unit 5 is closed to the fixed side, the first abutment region 59b abuts on the outer peripheral surface of the sheath 23. In consequence, the probe facing portion 55 abuts on the jaw facing portion 58, and an opening/closing angle α of the movable handle unit 5 to the fixed side is regulated so that the opening/closing angle α is minimize. The outer peripheral surface of the sheath 23 functions as a stopper that prevents the movable handle unit 5 from being closed more than necessary. When the first abutment region 59b abuts on the outer peripheral surface of the sheath 23, a minimum closing position of the movable handle unit 5 is determined.

As shown in FIG. 9C, when the movable handle unit 5 is opened to the fixed side, the second abutment region 59c abuts on the projecting portion 151. In consequence, the probe facing portion 55 opens to the jaw facing portion 58, and the opening/closing angle α of the movable handle unit 5 to the fixed side is regulated so that the opening/closing angle α is maximize. The projecting portion 151 functions as a stopper that prevents the movable handle unit 5 from being opened more than necessary. When the second abutment region 59c abuts on the projecting portion 151, a maximum opening position of the movable handle unit 5 is determined.

In this way, the first abutment region 59b abuts on the outer peripheral surface of the sheath 23 and the second abutment region 59c abuts on the projecting portion 151, whereby the opening/closing angle α of the movable handle unit 5 to the fixed side is regulated. Furthermore, the movable handle unit 5 is prevented from being opened or closed more than necessary, and the opening/closing position of the movable handle unit 5 to the fixed side is determined. Such regulating and positioning are performed in conjunction with a rotating operation of the movable handle unit 5.

[Effect]

In the present embodiment, by the sheath 23, the projecting portion 151, the first abutment region 59b and the second abutment region 59c as the regulating mechanism 150, the opening/closing angle α of the movable handle unit 5 to the fixed side can be regulated, the movable handle unit 5 can be prevented from being opened or closed more than necessary, and the opening/closing position of the movable handle unit 5 to the fixed side can be determined.

In the present embodiment, the regulating mechanism 150 has the sheath 23, the projecting portion 151, the first abutment region 59b and the second abutment region 59c, but when the regulating and the positioning are performed in conjunction with the rotating operation of the movable handle unit 5, configuration members of the regulating mechanism 150 are not limited to these members.

Modification of Second Embodiment

[Configuration]

Only aspects different from the first and second embodiments will be described next, with reference to FIG. 10A, FIG. 10B and FIG. 10C. The present embodiment corresponds to a configuration shown in FIG. 7A and FIG. 7B.

A projecting portion 151 is provided more forward than an opening/closing axis member 100 in a longitudinal axis C direction.

As shown in FIG. 10B and FIG. 10C, a first abutment region 59b and a second abutment region 59c are provided around the opening/closing axis member 100 so that the first abutment region 59b and the second abutment region 59c are adjacent to the opening/closing axis member 100. Specifically, the first abutment region 59b and the second abutment region 59c are provided between the opening/closing axis member 100 and the projecting portion 151 in the longitudinal axis C direction.

As shown in FIG. 10B and FIG. 10C, an inner peripheral surface 59a further has a third abutment region 59d that abuts on an outer peripheral surface of a sheath 23 when a movable handle unit 5 opens to a fixed side and the second abutment region 59c accordingly abuts on the projecting portion 151.

As shown in FIG. 10B and FIG. 10C, the third abutment region 59d is provided on a side opposite to the first abutment region 59b via a through hole portion 59 in an opening/closing direction. The third abutment region 59d is provided in a distal end portion of the through hole portion 59. The third abutment region 59d includes an inner peripheral edge portion on a lower surface side of a jaw 52. The outer peripheral surface of the sheath 23 on which the third abutment region 59d abuts is a lower surface portion of the sheath 23 on a side opposite to an upper surface portion of the sheath 23.

[Operation]

As shown in FIG. 10B, when the movable handle unit 5 is closed to the fixed side, the first abutment region 59b abuts on the outer peripheral surface of the sheath 23. In consequence, a probe facing portion 55 abuts on a jaw facing portion 58, and an opening/closing angle α of the movable handle unit 5 to the fixed side is regulated so that the opening/closing angle α is minimize. The outer peripheral surface of the sheath 23 functions as a stopper that prevents the movable handle unit 5 from being closed more than necessary. When the first abutment region 59b abuts on the outer peripheral surface of the sheath 23, a minimum closing position of the movable handle unit 5 is determined.

As shown in FIG. 10C, when the movable handle unit 5 is opened to the fixed side, the second abutment region 59c abuts on the projecting portion 151, and simultaneously the third abutment region 59d abuts on the outer peripheral surface of the sheath 23. In consequence, the probe facing portion 55 opens to the jaw facing portion 58, and an opening/closing angle α of the movable handle unit 5 to the fixed side is regulated so that the opening/closing angle α is maximize. The projecting portion 151 and the outer peripheral surface of the sheath 23 function as a stopper that prevents the movable handle unit 5 from being opened more than necessary. When the second abutment region 59*c* abuts on the projecting portion 151 and the third abutment region 59*d* abuts on the outer peripheral surface of the sheath 23, a maximum opening position of the movable handle unit 5 is determined.

In this way, the first abutment region 59*b* abuts on the outer peripheral surface of the sheath 23, the second abutment region 59*c* abuts on the projecting portion 151 and the third abutment region 59*d* abuts on the outer peripheral surface of the sheath 23, whereby the opening/closing angle α of the movable handle unit 5 to the fixed side is regulated. Furthermore, the movable handle unit 5 is prevented from being opened or closed more than necessary, and the opening/closing position of the movable handle unit 5 to the fixed side is determined. Such regulating and positioning are performed in conjunction with a rotating operation of the movable handle unit 5.

[Effect]

In the present modification, by the sheath 23, the projecting portion 151, the first abutment region 59*b*, the second abutment region 59*c* and the third abutment region 59*d* as a regulating mechanism 150, the opening/closing angle α of the movable handle unit 5 to the fixed side can be regulated, the movable handle unit 5 can be prevented from being opened or closed more than necessary, and the opening/closing position of the movable handle unit 5 to the fixed side can be determined.

In the present modification, the regulating mechanism 150 has the sheath 23, the projecting portion 151, the first abutment region 59*b*, the second abutment region 59*c*, and the third abutment region 59*d*, but configuration members of the regulating mechanism 150 are not limited to these members, as long as the regulating and the positioning are performed in conjunction with the rotating operation of the movable handle unit 5.

The present invention is not limited to the above embodiments, and constituent elements can be modified to embody the present invention at the stage of implementation without departing from the gist of the invention. Various inventions can be formed by suitably combining the constituent elements disclosed in the above embodiments.

What is claimed is:

1. An energy treatment device comprising:
    a movable handle comprising a jaw and a first recess;
    an elongated member;
    a sheath comprising a hollow portion and a second recess, wherein the hollow portion is configured to receive the elongated member; and
    an axis member;
    wherein:
    the movable handle is assembled with the sheath to be rotatable about the axis member such that the jaw is openable and closeable with respect to the elongated member,
    a recess portion is formed by the first recess and the second recess when the movable handle is assembled with the sheath,
    the recess portion does not overlap with the hollow portion,
    the axis member is arranged in the recess portion, and
    $(D1+D2)/2 < L1$ is satisfied,
    where:
    D1 is a diameter of the hollow portion,
    D2 is a diameter of the first recess, and
    L1 is a distance between a central position of the hollow portion and a central position of the first recess in an opening/closing direction of the jaw.

2. The energy treatment device according to claim 1, wherein:
    the sheath comprises a sheath side attaching portion,
    the sheath side attaching portion is provided at a position offset from the hollow portion in an opening/closing direction of the jaw, and
    the second recess is provided in the sheath side attaching portion.

3. The energy treatment device according to claim 2, wherein:
    the movable handle comprises a jaw side attaching portion, and
    the first recess is provided in the jaw side attaching portion.

4. The energy treatment device according to claim 3, wherein:
    the first recess is a through hole which penetrates the jaw side attaching portion, and
    the through hole comprises a first hole portion in which the axis member is arranged, and a second hole portion in which the axis member is not arranged.

5. The energy treatment device according to claim 4, further comprising:
    a preventing member that prevents the axis member from falling out of the through hole,
    wherein the preventing member is arranged in the second hole portion.

* * * * *